US012678034B2

(12) United States Patent
Hirano et al.

(10) Patent No.: US 12,678,034 B2
(45) Date of Patent: Jul. 14, 2026

(54) IMAGING DEVICE, ENDOSCOPE, IMAGING SYSTEM, AND IMAGING METHOD

(71) Applicant: OLYMPUS MEDICAL SYSTEMS CORP., Hachioji (JP)

(72) Inventors: Mayu Hirano, Tachikawa (JP); Takanori Tanaka, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 117 days.

(21) Appl. No.: 18/748,401

(22) Filed: Jun. 20, 2024

(65) Prior Publication Data

US 2024/0423462 A1     Dec. 26, 2024

Related U.S. Application Data

(60) Provisional application No. 63/523,266, filed on Jun. 26, 2023.

(51) Int. Cl.
*A61B 1/05*          (2006.01)
*H04N 25/00*       (2023.01)

(52) U.S. Cl.
CPC ............. *A61B 1/051* (2013.01); *H04N 25/00* (2023.01)

(58) Field of Classification Search
CPC ........ H04N 25/78; H04N 25/00; H04N 25/42; H04N 25/441; H04N 23/555; A61B 1/051; A61B 1/05
USPC ..... 348/65, 45, 46, 294, 298–304, 308, 309, 348/311, 312
See application file for complete search history.

(56) References Cited

U.S. PATENT DOCUMENTS

2016/0150176 A1* 5/2016 Hiyama ................. H04N 25/77
                                                                           348/301

FOREIGN PATENT DOCUMENTS

JP          6064097 B2    1/2017
JP          6089716 B2    3/2017

* cited by examiner

*Primary Examiner* — Sherrie Hsia
(74) *Attorney, Agent, or Firm* — WHDA, LLP

(57)          ABSTRACT
An imaging device includes multiple pixels. When a first mode is set, at least one pixel of the multiple pixels sets a state of a transfer switch to an ON state and outputs a first pixel signal in accordance with an electric charge held in a floating diffusion. When a second mode is set, the at least one pixel sets the state of the transfer switch to an OFF state, sets a state of the reset switch to the ON state, and outputs a second pixel signal in accordance with the electric charge held in the floating diffusion in an output period.

11 Claims, 9 Drawing Sheets

21; TIMING GENERATOR

10

20; IMAGING UNIT

22; VERTICAL SELECTION CIRCUIT

26; PIXEL

30

23; COLUMN CIRCUIT UNIT

27; COLUMN CIRCUIT

25; OUTPUT UNIT

28

24

HORIZONTAL SELECTION CIRCUIT

ImageArea1[x, y]

ImageArea2[x, y]

FIRST PIXEL
SIGNAL

SECOND PIXEL
SIGNAL

N ROWS

1 FRAME

CORRECTION

FIRST PIXEL
SIGNAL

1 FRAME

SECOND PIXEL
SIGNAL

X COLUMNS

IMAGING DEVICE, ENDOSCOPE, IMAGING SYSTEM, AND IMAGING METHOD

Priority is claimed on U.S. Provisional Patent Application No. 63/523,266, filed on Jun. 26, 2023, the content of which is incorporated herein by reference.

BACKGROUND OF THE INVENTION

Field of the Invention

The present invention relates to an imaging device, an endoscope, an imaging system, and an imaging method.

Description of Related Art

An image sensor includes two or more pixels disposed in a matrix shape. Each pixel includes a photoelectric conversion element, a floating diffusion (FD), a transfer switch, a reset switch, and the like. The photoelectric conversion element receives light and generates an electric charge in accordance with the amount of the light. The FD holds the electric charge generated by the photoelectric conversion element. The transfer switch transfers the electric charge generated by the photoelectric conversion element to the FD. The reset switch resets the electric charge held in the FD.

Image sensors including optical black (OB) pixels in addition to effective pixels have been developed. The OB pixels are light-shielded. A pixel value of an effective pixel of each column is corrected by using a signal output from an OB pixel of each column. Japanese Patent No. 6064097 discloses an image sensor that uses dummy pixels instead of OB pixels.

On the other hand, Japanese Patent No. 6089716 discloses a method of correcting a pixel value of an effective pixel without using an OB pixel or a dummy pixel. According to the method, an image sensor operates in a normal output mode or a dummy black level output mode. In the normal output mode, a pixel value used for correction is generated when no light is incident on pixels of the image sensor. In the dummy black level output mode, a pixel value used for correction is generated when light is incident on the pixels.

In the normal output mode, a reset switch is turned on first, and an electric charge of an FD is reset. After the reset switch is turned off, a transfer switch is turned on and an electric charge accumulated in a photoelectric conversion element is transferred to the FD. After the transfer switch is turned off, a signal is output in accordance with the electric charge of the FD.

In the dummy black level output mode, the reset switch is turned on first, and an electric charge of the FD is reset. After the reset switch is turned off, the reset switch instead of the transfer switch is turned on again. After the reset switch is turned off, a signal is output in accordance with the electric charge of the FD.

SUMMARY OF THE INVENTION

According to a first aspect of the present invention, an imaging device includes multiple pixels disposed in a matrix shape. Each of the multiple pixels includes a photoelectric conversion element, a floating diffusion, a transfer switch, and a reset switch. The photoelectric conversion element is configured to perform photoelectric conversion and generate an electric charge in accordance with the amount of received light. The floating diffusion is configured to hold the electric charge. The transfer switch is configured to transfer the electric charge generated by the photoelectric conversion element to the floating diffusion. The reset switch is configured to reset the electric charge held in the floating diffusion. The state of each of the transfer switch and the reset switch is switchable between an ON state and an OFF state. An operation mode that is switchable between a first mode and a second mode is set. When the first mode is set, at least one pixel sets the state of the transfer switch to the ON state so as to transfer the electric charge to the floating diffusion and outputs a first pixel signal in accordance with the electric charge held in the floating diffusion. After the electric charge is transferred to the floating diffusion, the at least one pixel sets the state of the transfer switch to the OFF state so as to stop transfer of the electric charge to the floating diffusion. When the second mode is set, the at least one pixel sets the state of the reset switch to the ON state so as to reset the electric charge held in the floating diffusion, fixes the state of the transfer switch to the OFF state, and outputs a second pixel signal in accordance with the electric charge held in the floating diffusion in an output period. The state of the reset switch in the at least one pixel is fixed to the ON state in the output period.

According to a second aspect of the present invention, in the first aspect, each of the multiple pixels may include a selection switch that includes a gate terminal and is configured to output the first pixel signal or the second pixel signal when a row selection signal is input to the gate terminal.

According to a third aspect of the present invention, in the first aspect, the imaging device may include a signal-holding circuit configured to hold the second pixel signal. The output period may include a period during which the signal-holding circuit holds the second pixel signal.

According to a fourth aspect of the present invention, in the first aspect, the state of the transfer switch in the at least one pixel may be fixed to the OFF state in the output period.

According to a fifth aspect of the present invention, in the first aspect, each of two or more vertical scanning periods of the imaging device may include a first period during which the first mode is set and a second period during which the second mode is set.

According to a sixth aspect of the present invention, in the first aspect, the second mode may be set in at least one vertical scanning period of two or more vertical scanning periods of the imaging device.

According to a seventh aspect of the present invention, an endoscope includes both a scope to be inserted into a living body and the imaging device. The imaging device is disposed in the distal end of the scope.

According to an eighth aspect of the present invention, an imaging system includes an imaging device and a correction circuit. The correction circuit is configured to receive the first pixel signal and the second pixel signal and correct the first pixel signal by using the second pixel signal.

According to a ninth aspect of the present invention, in the eighth aspect, the correction circuit may be configured to: receive the first pixel signal and the second pixel signal output from the at least one pixel in a first period during which no light is incident on the multiple pixels; receive the first pixel signal and the second pixel signal output from the at least one pixel in a second period different from the first period; perform correction using the second pixel signal of the first period on the first pixel signal of the first period so as to generate a reference pixel signal; correct the first pixel signal of the second period by using the second pixel signal of the second period; and correct the corrected first pixel signal of the second period by using the reference pixel signal.

According to a tenth aspect of the present invention, in the eighth aspect, the correction circuit may be configured to correct the first pixel signal by using the second pixel signal output from a pixel disposed in at least one row among the multiple pixels.

According to an eleventh aspect of the present invention, an imaging method uses an imaging device that includes multiple pixels disposed in a matrix shape. The imaging method includes an imaging step. Each of the multiple pixels includes a photoelectric conversion element, a floating diffusion, a transfer switch, and a reset switch. The photoelectric conversion element is configured to perform photoelectric conversion and generate an electric charge in accordance with the amount of received light. The floating diffusion is configured to hold the electric charge. The transfer switch is configured to transfer the electric charge generated by the photoelectric conversion element to the floating diffusion. The reset switch is configured to reset the electric charge held in the floating diffusion. The state of each of the transfer switch and the reset switch is switchable between an ON state and an OFF state. An operation mode that is switchable between a first mode and a second mode is set. The imaging step includes the following: setting the state of the transfer switch of at least one pixel to the ON state so as to transfer the electric charge to the floating diffusion when the first mode is set; outputting a first pixel signal in accordance with the electric charge held in the floating diffusion when the first mode is set; setting the state of the transfer switch of the at least one pixel to the OFF state so as to stop transfer of the electric charge to the floating diffusion after the electric charge is transferred to the floating diffusion; setting the state of the reset switch of the at least one pixel to the ON state so as to reset the electric charge held in the floating diffusion when the second mode is set; and outputting a second pixel signal in accordance with the electric charge held in the floating diffusion in an output period. When the second mode is set, the state of the transfer switch of the at least one pixel is fixed to the OFF state. The state of the reset switch in the at least one pixel is fixed to the ON state in the output period.

BRIEF DESCRIPTION OF THE DRAWINGS

FIG. 11 is a diagram showing an example of a reference pixel signal in the second modified example of the embodiment of the present invention.

DETAILED DESCRIPTION OF THE INVENTION

Embodiments of the present invention will be described with reference to the drawings. Hereinafter, an example of an endoscope system including an imaging device will be described.

Figure 1:
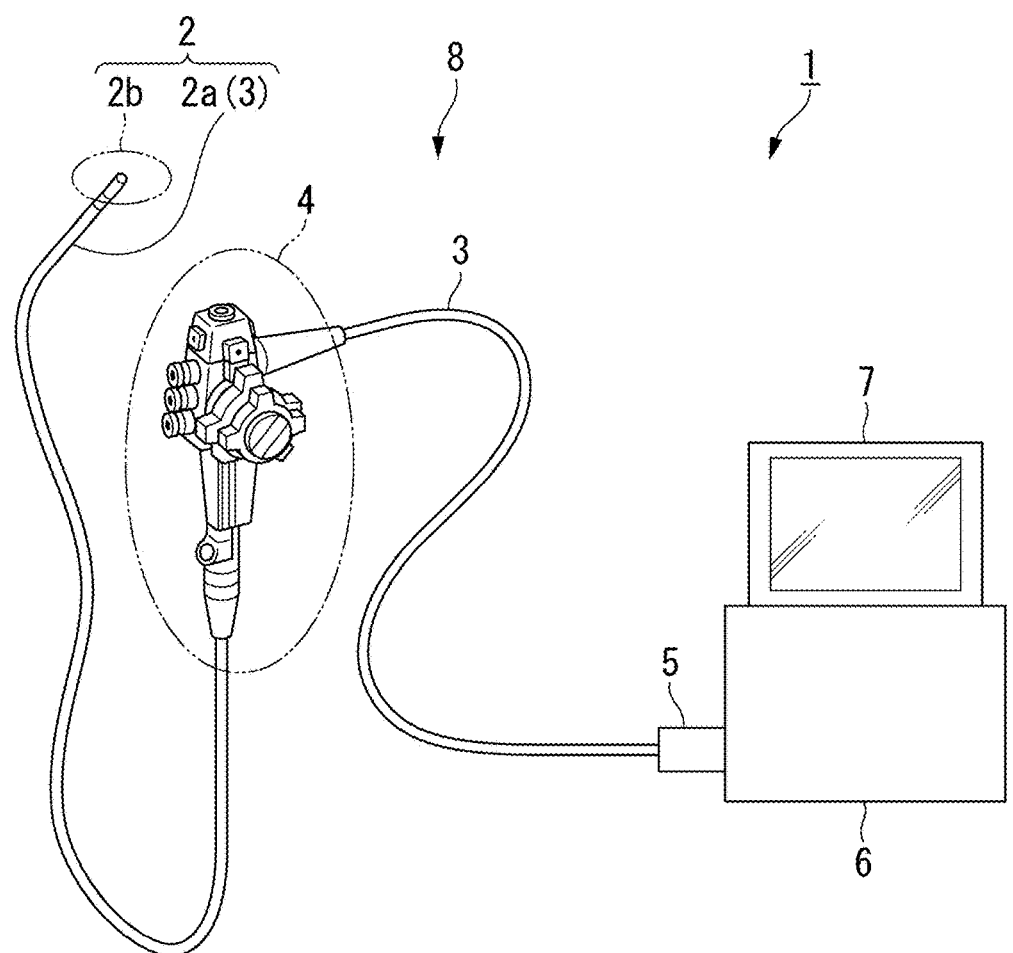
FIG. 1 is a schematic diagram showing a configuration of an endoscope system according to an embodiment of the present invention.

FIG. 1 shows a configuration of an endoscope system 1 (imaging system) according to an embodiment of the present invention. The endoscope system 1 shown in FIG. 1 includes an endoscope insertion unit 2, a transmission cable 3, an operation unit 4, a connector unit 5, a control unit 6, and a display device 7. The endoscope insertion unit 2, the transmission cable 3, the operation unit 4, and the connector unit 5 constitute a scope 8 (endoscope).

Figure 2:
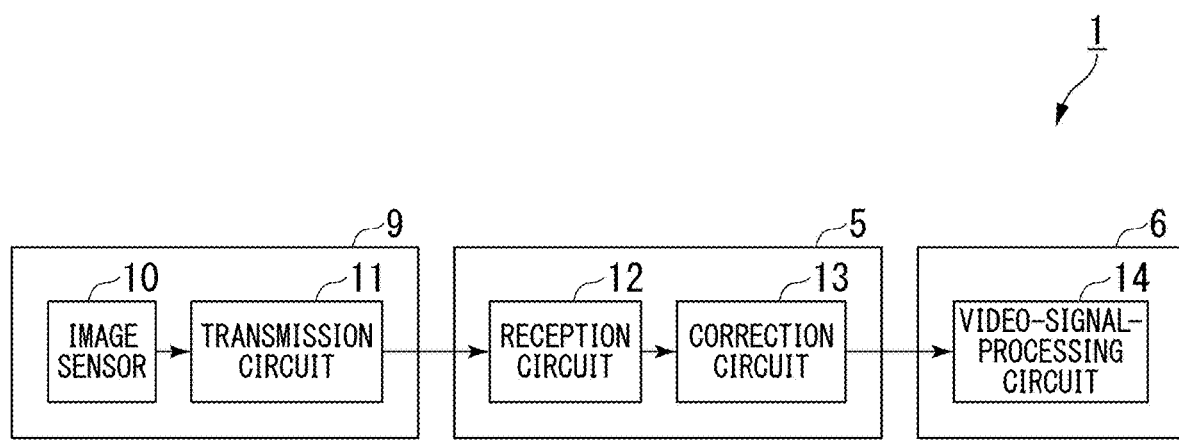
FIG. 2 is a block diagram showing a configuration of a camera unit, a connector unit, and a control unit included in the endoscope system according to the embodiment of the present invention.

The endoscope insertion unit 2 includes an insertion unit 2a. The insertion unit 2a is part of the transmission cable 3. The insertion unit 2a is to be inserted inside a living body, which is a subject. The endoscope insertion unit 2 generates a pixel signal by imaging the inside of the subject. The endoscope insertion unit 2 outputs the generated pixel signal to the control unit 6. A camera unit 9 shown in FIG. 2 is disposed in a distal end 2b of the insertion unit 2a. In the insertion unit 2a, the operation unit 4 is connected to the end part opposite the distal end 2b. The operation unit 4 receives various operations for the endoscope insertion unit 2 from a user.

The transmission cable 3 connects the camera unit 9 and the connector unit 5. The pixel signal generated by the camera unit 9 is output to the connector unit 5 via the transmission cable 3.

The connector unit 5 is connected to the transmission cable 3 and the control unit 6. The connector unit 5 performs predetermined processing on the pixel signal output from the endoscope insertion unit 2 and generates a video signal. The connector unit 5 outputs the video signal to the control unit 6.

The control unit 6 performs image processing on the video signal output from the connector unit 5. Furthermore, the control unit 6 centrally controls the entire endoscope system 1.

The display device 7 displays a video based on the video signal processed by the control unit 6. In addition, the display device 7 displays various kinds of information related to the endoscope system 1.

The endoscope system 1 includes the camera unit 9, the connector unit 5, and the control unit 6 shown in FIG. 2. FIG. 2 shows a configuration of the camera unit 9, the connector unit 5, and the control unit 6. The camera unit 9 is disposed in the distal end 2b of the scope 8. The operation unit 4 and the display device 7 are not shown in FIG. 2.

The endoscope system 1 includes a light source device that generates illumination light emitted to the subject. The light source device is not shown in FIG. 2.

The camera unit 9 includes an image sensor 10 and a transmission circuit 11. The connector unit 5 includes a reception circuit 12 and a correction circuit 13. The control unit 6 includes a video-processing circuit 14.

The image sensor 10 generates a pixel signal and outputs the pixel signal to the transmission circuit 11. The transmission circuit 11 transmits the pixel signal to the connector unit 5. The reception circuit 12 receives the pixel signal and outputs the pixel signal to the correction circuit 13. The correction circuit 13 corrects the pixel signal by using a method described later and generates a video signal. The correction circuit 13 outputs the video signal to the control unit 6. The video-processing circuit 14 performs predetermined signal processing on the video signal and outputs the video signal to the display device 7.

The correction circuit 13 or the video-processing circuit 14 may be configured as a digital circuit including at least one of a processor and a logic circuit. For example, the processor is a central processing unit (CPU). For example, the logic circuit is at least one of an application-specific integrated circuit (ASIC) and a field-programmable gate array (FPGA). The correction circuit 13 or the video-processing circuit 14 may include one or a plurality of processors. The correction circuit 13 or the video-processing circuit 14 may include one or a plurality of logic circuits.

A computer of the connector unit 5 or the control unit 6 may read a program and execute the read program. The program includes commands defining the operations of the correction circuit 13 or the video-processing circuit 14. In other words, the functions of the correction circuit 13 or the video-processing circuit 14 may be realized by software. The program may be transmitted from a computer storing the program to the connector unit 5 or the control unit 6 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

Figure 3:
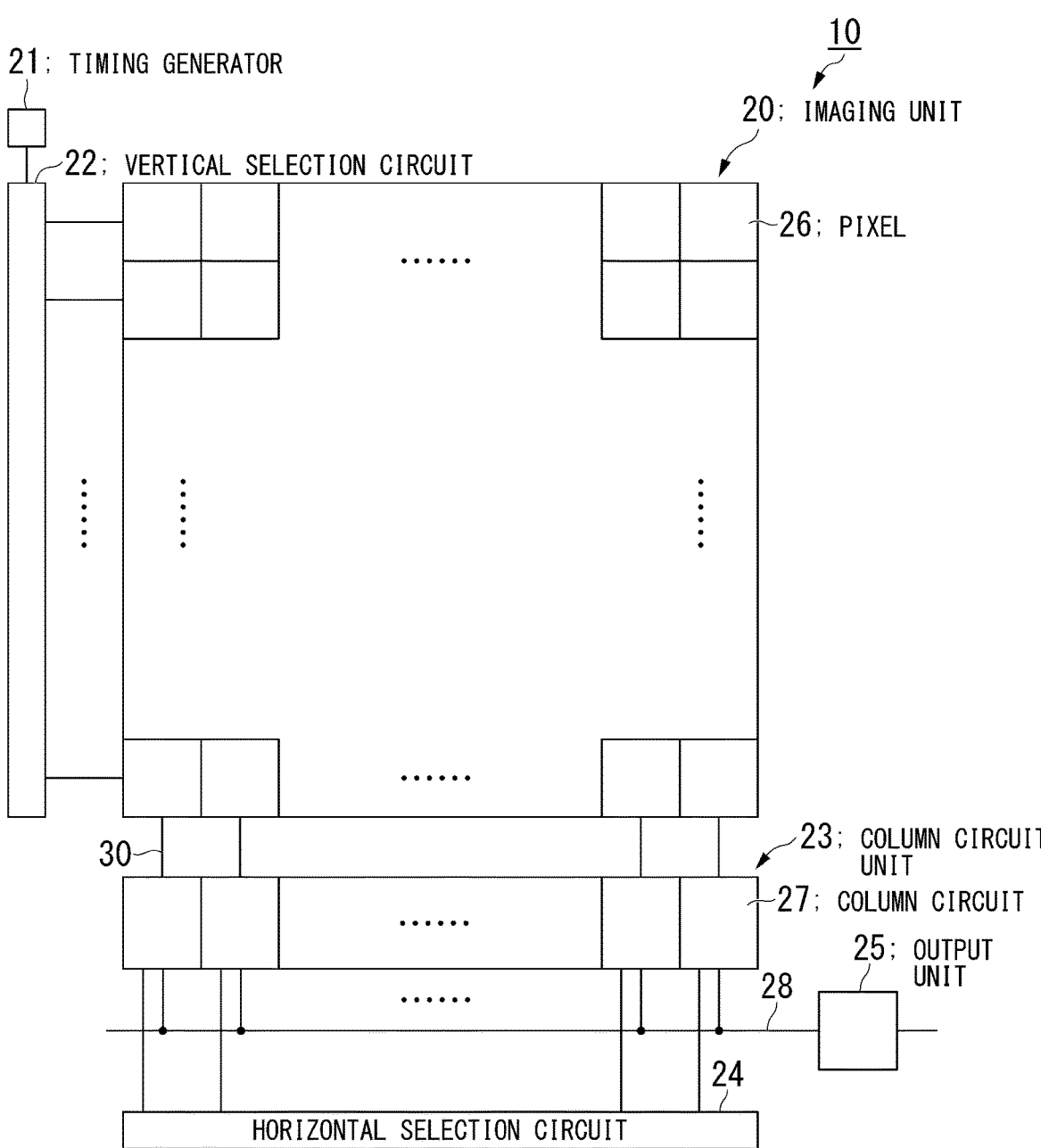
FIG. 3 is a block diagram showing a configuration of an image sensor included in the endoscope system according to the embodiment of the present invention.

FIG. 3 shows a configuration of the image sensor 10. The image sensor 10 includes an imaging unit 20, a timing generator 21, a vertical selection circuit 22, a column circuit unit 23, a horizontal selection circuit 24, and an output unit 25.

The imaging unit 20 includes two or more pixels 26 disposed in a matrix shape. The two or more pixels 26 constitute an array having m rows and n columns. The number (m) of rows is two or more, and the number (n) of columns is two or more. The number of rows and the number of columns are not necessarily the same. Each pixel 26 outputs a first pixel signal having a signal level and a second pixel signal having a reset level.

The timing generator 21 generates a timing signal and outputs the timing signal to the vertical selection circuit 22. The vertical selection circuit 22 selects pixels 26 disposed in the row direction in the array of the two or more pixels 26. The vertical selection circuit 22 controls the operations of the selected pixels 26. The vertical selection circuit 22 outputs control signals used for controlling the two or more pixels 26 for each row in the array of the two or more pixels 26.

The column circuit unit 23 includes two or more column circuits 27. Each column circuit 27 is disposed for each column in the array of the two or more pixels 26. Each column circuit 27 is connected to a vertical signal line 30 extending in the vertical direction, that is, the column direction. The vertical signal line 30 is disposed for each column in the array of the two or more pixels 26. The vertical signal line 30 is connected to pixels 26 of each column. Each column circuit 27 is electrically connected to each pixel 26 via the vertical signal line 30. Each column circuit 27 holds the first pixel signal and the second pixel signal output from each pixel 26.

Each column circuit 27 is connected to a horizontal signal line 28 extending in the horizontal direction, that is, the row direction. A selection pulse is output from the horizontal selection circuit 24 to each column circuit 27. The column circuit 27 selected based on the selection pulse outputs the first pixel signal and the second pixel signal to the horizontal signal line 28.

One column circuit 27 may be disposed for two or more columns in the array of the two or more pixels 26 and may be used in the two or more columns in a time-division manner. Accordingly, the column circuit 27 has only to be disposed so as to correspond to one or more columns in the array of the two or more pixels 26.

The horizontal signal line 28 is connected to the output unit 25. The horizontal selection circuit 24 sequentially selects the column circuits 27 by sequentially outputting selection pulses to the column circuits 27. The first pixel signal and the second pixel signal output from the column circuit 27 selected by the horizontal selection circuit 24 are transferred to the output unit 25. The output unit 25 outputs the first pixel signal and the second pixel signal to the transmission circuit 11.

An operation mode that is switchable between a first mode and a second mode is set in the image sensor 10. When the first mode is set in the image sensor 10, each pixel 26 generates a first pixel signal. When the second mode is set in the image sensor 10, each pixel 26 generates a second pixel signal.

Figure 4:
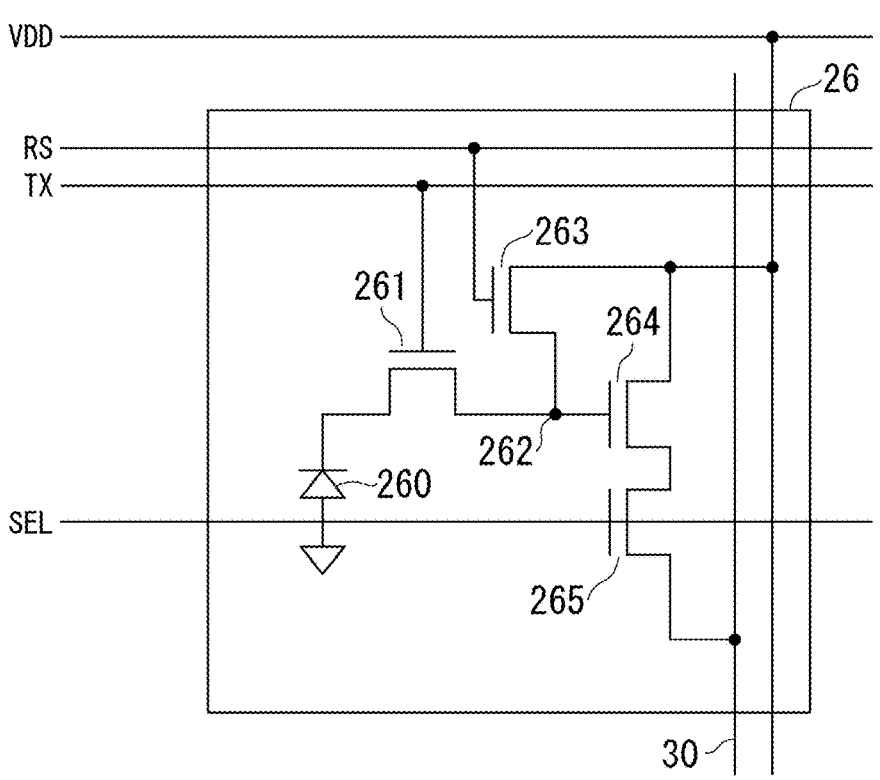
FIG. 4 is a diagram showing a configuration of a pixel in the image sensor included in the endoscope system according to the embodiment of the present invention.

FIG. 4 shows a configuration of each pixel 26. The pixel 26 shown in FIG. 4 includes a photoelectric conversion element 260, a transfer switch 261, a floating diffusion (FD) 262, a reset switch 263, an amplification circuit 264, and a selection switch 265.

The photoelectric conversion element 260 is a photodiode. The photoelectric conversion element 260 performs photoelectric conversion on light incident thereon the photoelectric conversion element 260 and generates an electric charge in accordance with the amount of the light. The transfer switch 261 transfers the electric charge generated by the photoelectric conversion element 260 to the FD 262. The FD 262 holds the electric charge transferred by the transfer switch 261.

The reset switch 263 resets the voltage of the FD 262 to a voltage in accordance with a power source voltage VDD. By doing this, the reset switch 263 resets the electric charge held in the FD 262. The amplification circuit 264 amplifies a signal based on the voltage of the FD 262, thus generating a pixel signal. The selection switch 265 outputs the pixel signal to the vertical signal line 30. A first pixel signal having a signal level and a second pixel signal having a reset level are output from the pixel 26.

The vertical selection circuit 22 outputs a reset control signal RS, a transfer control signal TX, and a selection control signal SEL. These signals are output for each row in the array of the two or more pixels 26. The reset control signal RS is input to the gate terminal of the reset switch 263. The transfer control signal TX is input to the gate terminal of the transfer switch 261. The selection control signal SEL is input to the gate terminal of the selection switch 265.

The transfer switch 261, the reset switch 263, the amplification circuit 264, and the selection switch 265 are transistors. The state of each of the transfer switch 261, the reset switch 263, and the selection switch 265 becomes either an ON state or an OFF state. Each switch can switch between the ON state and the OFF state.

The state of the reset switch 263 is controlled in accordance with the reset control signal RS. The state of the transfer switch 261 is controlled in accordance with the transfer control signal TX. The state of the selection switch 265 is controlled in accordance with the selection control signal SEL.

Figure 5:
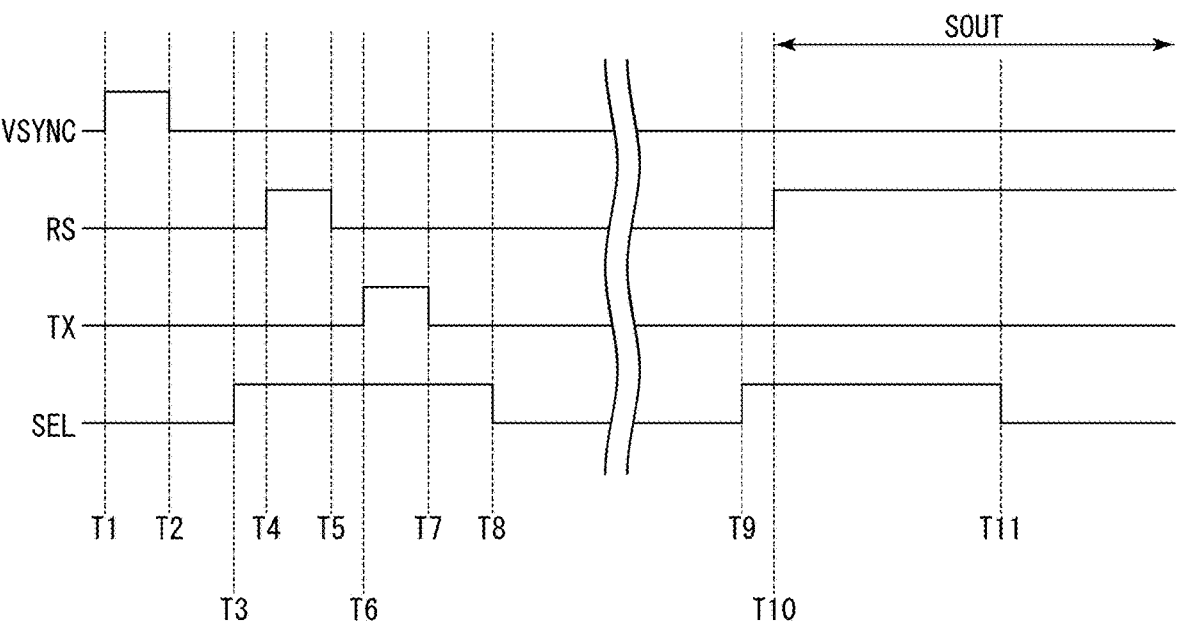
FIG. 5 is a timing chart showing waveforms of signals in the image sensor included in the endoscope system according to the embodiment of the present invention.

FIG. 5 shows waveforms of a vertical synchronization signal VSYNC, the reset control signal RS, the transfer control signal TX, and the selection control signal SEL. The horizontal direction in FIG. 5 indicates time, and the vertical direction in FIG. 5 indicates a voltage value of each signal. An operation of a pixel 26 will be described by using FIG. 5.

The vertical synchronization signal VSYNC is output from the timing generator 21 to the vertical selection circuit 22. The vertical synchronization signal VSYNC indicates a start timing and an end timing of a vertical scanning period. Each of the vertical synchronization signal VSYNC, the reset control signal RS, the transfer control signal TX, and the selection control signal SEL has a high (H) voltage or a low (L) voltage.

Before a timing T1, the voltage of each of the vertical synchronization signal VSYNC, the reset control signal RS, the transfer control signal TX, and the selection control signal SEL is the L voltage. The state of each of the reset switch 263, the transfer switch 261, and the selection switch 265 is the OFF state.

At the timing T1, the voltage of the vertical synchronization signal VSYNC changes from the L voltage to the H voltage. At this time, a new vertical scanning period is started. In addition, a vertical scanning period prior to the new vertical scanning period is completed. The operation mode of the image sensor 10 is set to the first mode. At a timing T2 after the timing T1, the voltage of the vertical synchronization signal VSYNC changes from the H voltage to the L voltage.

At a timing T3 after the timing T2, the voltage of the selection control signal SEL changes from the L voltage to the H voltage. Therefore, the state of the selection switch 265 changes from the OFF state to the ON state. At this time, the amplification circuit 264 and the vertical signal line 30 are electrically connected.

At a timing T4 after the timing T3, the voltage of the reset control signal RS changes from the L voltage to the H voltage. Therefore, the state of the reset switch 263 changes from the OFF state to the ON state. At this time, the reset switch 263 resets the electric charge held in the FD 262. At a timing T5 after the timing T4, the voltage of the reset control signal RS changes from the H voltage to the L voltage. Therefore, the state of the reset switch 263 changes from the ON state to the OFF state.

At a timing T6 after the timing T5, the transfer control signal TX changes from the L voltage to the H voltage. Therefore, the state of the transfer switch 261 changes from the OFF state to the ON state. At this time, the transfer switch 261 transfers the electric charge generated by the photoelectric conversion element 260 to the FD 262. The FD 262 holds the electric charge transferred by the transfer switch 261. At a timing T7 after the timing T6, the transfer control signal TX changes from the H voltage to the L voltage. Therefore, the state of the transfer switch 261 changes from the ON state to the OFF state.

The amplification circuit 264 amplifies a signal based on the voltage of the FD 262, thus generating a first pixel signal. The selection switch 265 outputs the first pixel signal to the vertical signal line 30. Since the selection control signal SEL is output to all the pixels 26 of one row, each of the pixels 26 outputs the first pixel signal to the vertical signal line 30 disposed in a column corresponding to each of the pixels 26. The first pixel signal is output to a column circuit 27 of each column by the vertical signal line 30. The column circuit 27 includes a capacitor and holds the first pixel signal in the capacitor.

At a timing T8 after the timing T7, the voltage of the selection control signal SEL changes from the H voltage to the L voltage. Therefore, the state of the selection switch 265 changes from the ON state to the OFF state.

The horizontal selection circuit 24 outputs a selection pulse to a column circuit 27 of a first column. At this time, the column circuit 27 of the first column outputs the first pixel signal to the horizontal signal line 28. Thereafter, the horizontal selection circuit 24 outputs a selection pulse to a column circuit 27 of a second column different from the first column. At this time, the column circuit 27 of the second column outputs the first pixel signal to the horizontal signal line 28. This operation is repeated, and the first pixel signals in all the columns are sequentially output to the horizontal signal line 28 and are sequentially transferred to the output unit 25.

The output unit 25 outputs the first pixel signals to the transmission circuit 11. The transmission circuit 11 transmits the first pixel signals to the connector unit 5. The reception circuit 12 receives the first pixel signals and outputs the first pixel signals to the correction circuit 13.

The operation from the timing T3 to the timing T8 is executed in pixels 26 of a first row in the imaging unit 20. Thereafter, the operation from the timing T3 to the timing T8 is executed in pixels 26 of a second row different from the first row. This operation is repeated, and the operation from the timing T3 to the timing T8 is executed in pixels 26 of all the rows.

After the operation from the timing T3 to the timing T8 is executed in the pixels 26 of all the rows, the operation mode of the image sensor 10 is changed from the first mode to the second mode.

After the operation mode of the image sensor 10 is changed to the second mode, the voltage of the selection control signal SEL changes from the L voltage to the H voltage at a timing T9. Therefore, the state of the selection switch 265 changes from the OFF state to the ON state. At this time, the amplification circuit 264 and the vertical signal line 30 are electrically connected.

At a timing T10 after the timing T9, the voltage of the reset control signal RS changes from the L voltage to the H voltage. Therefore, the state of the reset switch 263 changes from the OFF state to the ON state. At this time, the reset switch 263 resets the electric charge held in the FD 262. An output period SOUT is started at the timing T10. In the output period SOUT, the state of the reset switch 263 is fixed to the ON state. In addition, when the operation mode of the image sensor 10 is the second mode, the state of the transfer switch 261 is fixed to the OFF state. Therefore, the transfer of the electric charge from the photoelectric conversion element 260 to the FD 262 is stopped.

The amplification circuit 264 amplifies a signal based on the voltage of the FD 262, thus generating a second pixel signal. The selection switch 265 outputs the second pixel signal to the vertical signal line 30. Since the selection control signal SEL is output to all the pixels 26 of one row, each of the pixels 26 outputs the second pixel signal to the vertical signal line 30 disposed in a column corresponding to each of the pixels 26. The second pixel signal is output to a column circuit 27 of each column by the vertical signal line 30. The column circuit 27 includes holds the second pixel signal in the capacitor.

At a timing T11 after the timing T10, the voltage of the selection control signal SEL changes from the H voltage to the L voltage. Therefore, the state of the selection switch 265 changes from the ON state to the OFF state.

The horizontal selection circuit 24 outputs a selection pulse to a column circuit 27 of a first column. At this time, the column circuit 27 of the first column outputs the second pixel signal to the horizontal signal line 28. Thereafter, the horizontal selection circuit 24 outputs a selection pulse to a column circuit 27 of a second column different from the first column. At this time, the column circuit 27 of the second column outputs the second pixel signal to the horizontal signal line 28. This operation is repeated, and the second pixel signals in all the columns are sequentially output to the horizontal signal line 28 and are sequentially transferred to the output unit 25.

The output unit 25 outputs the second pixel signals to the transmission circuit 11. The transmission circuit 11 transmits the second pixel signals to the connector unit 5. The reception circuit 12 receives the second pixel signals and outputs the second pixel signals to the correction circuit 13.

The operation from the timing T9 to the timing T11 is executed in pixels 26 of a first row in the imaging unit 20. Thereafter, the operation from the timing T9 to the timing T11 is executed in pixels 26 of a second row different from the first row. This operation is repeated, and the operation from the timing T9 to the timing T11 is executed in pixels 26 of all the rows.

The states of the reset switches 263 of the pixels 26 of the N-th row are maintained to the ON state until all the second pixel signals output from the pixels 26 are output to the horizontal signal line 28. After all the second pixel signals of the N-th row are output to the horizontal signal line 28, the voltage of the reset control signal RS changes from the H voltage to the L voltage. Therefore, the state of the reset switch 263 changes from the ON state to the OFF state. At this time, the output period SOUT is completed.

The operation shown in FIG. 5 is executed in one vertical scanning period. The first pixel signal and the second pixel signal are output from each pixel 26 in one vertical scanning period. The operation shown in FIG. 5 is repeated in two or more vertical scanning periods.

The operation mode of the image sensor 10 may be set to the second mode in only some of the two or more vertical scanning periods. The operation mode of the image sensor 10 may be set only to the first mode in some of the two or more vertical scanning periods.

In the operation shown in FIG. 5, the state of the reset switch 263 is fixed to the ON state in the output period SOUT. In a case in which strong light is incident on the imaging unit 20, the electric charge that has overflowed from the photoelectric conversion element 260 and has flowed in the FD 262 is reset by the reset switch 263. Therefore, each pixel 26 can output a second pixel signal having a fixed level. Each pixel 26 can output the same second pixel signal as that obtained when no light is incident on the imaging unit 20.

The correction circuit 13 corrects a first pixel signal by using a second pixel signal. Processing executed by the correction circuit 13 will be described.

Figure 6:
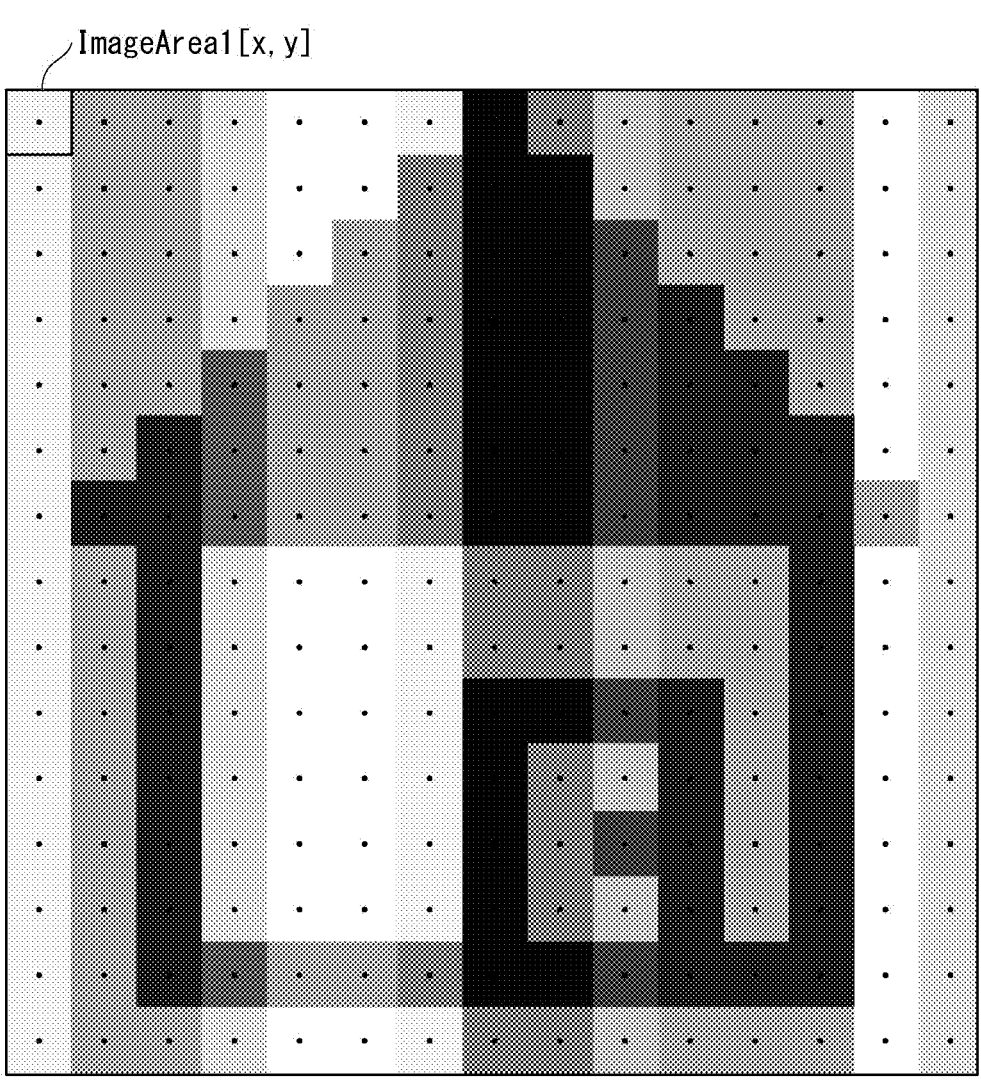
FIG. 6 is a diagram showing an example of a first pixel signal in the embodiment of the present invention.
Figure 7:
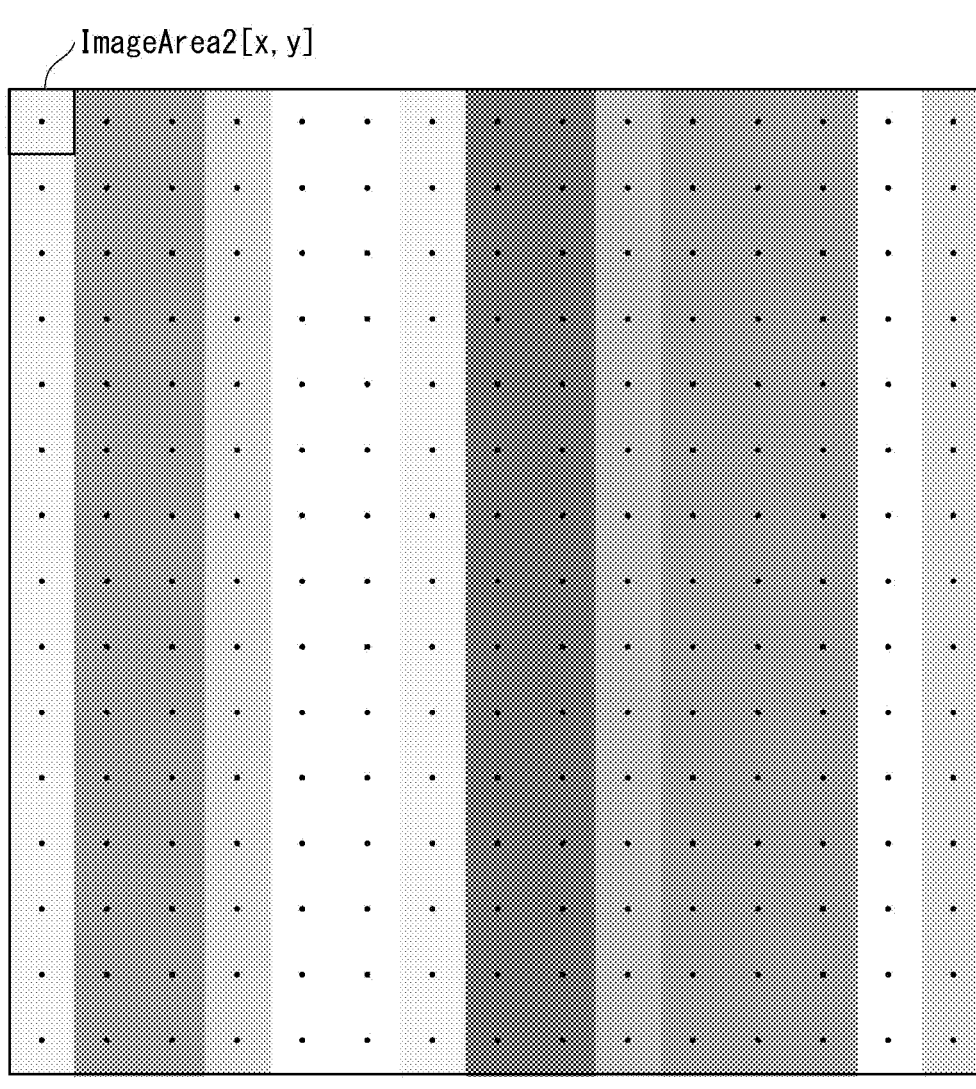
FIG. 7 is a diagram showing an example of a second pixel signal in the embodiment of the present invention.

FIG. 6 shows an example of the first pixel signal. Values of first pixel signals output from pixels 26 of 15 rows and 15 columns are shown in FIG. 6. FIG. 7 shows an example of the second pixel signal. Values of second pixel signals output from the pixels 26 of the 15 rows and the 15 columns are shown in FIG. 7. The first pixel signals and the second pixel signals include vertical-line-shaped noise.

The correction circuit 13 calculates an average value Col1[x] of values of second pixel signals of each column in accordance with the following Expression (1). ImageArea2 [x, y] in Expression (1) indicates a value of a second pixel signal of a pixel 26 of the x-th column and the y-th row.

[Math. 1]

$$Col1[x] = \frac{1}{n}\sum_{y=0}^{n-1} ImageArea'[x, y] \tag{1}$$

n in Expression (1) indicates the number of rows. When the number of rows in the imaging unit 20 is K, n in Expression (1) is 1 or more and K or less.

The correction circuit 13 calculates a correction value ImageArea1[x, y] of a first pixel signal of the pixel 26 of the x-th column and the y-th row in accordance with the following Expression (2). ImageArea1[x, y] in Expression (2) indicates the value of the first pixel signal of the pixel 26 of the x-th column and the y-th row.

$$ImageArea[x, y] = ImageArea1[x, y] - Col1[x] \tag{2}$$

As shown in Expression (2), the correction circuit 13 subtracts the value of the second pixel signal from the value of the first pixel signal, thus correcting the value of the first pixel signal. The correction circuit 13 generates a video signal based on the corrected first pixel signal and outputs the video signal to the control unit 6.

Figure 8:
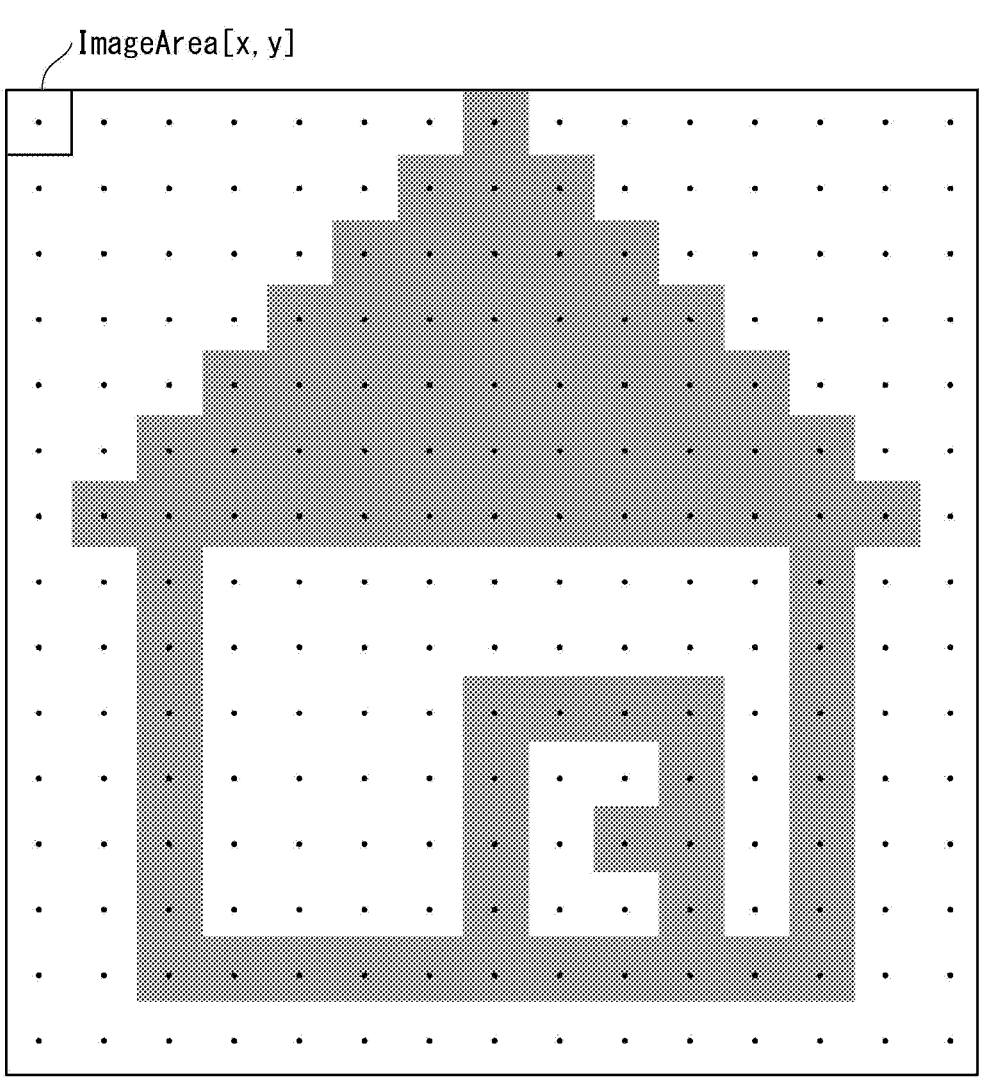
FIG. 8 is a diagram showing an example of a corrected first pixel signal in the embodiment of the present invention.

FIG. 8 shows an example of the corrected first pixel signal. The correction circuit 13 subtracts the value of the second pixel signal shown in FIG. 7 from the value of the first pixel signal shown in FIG. 6, thus calculating the value of the first pixel signal shown in FIG. 8. Vertical-line-shaped noise in the first pixel signals shown in FIG. 6 is eliminated.

The first pixel signal and the second pixel signal used by the correction circuit 13 need not be generated in the same vertical scanning period. The correction circuit 13 may use a first pixel signal generated in a first vertical scanning period and a second pixel signal generated in a second vertical scanning period different from the first vertical scanning period. The first vertical scanning period and the second vertical scanning period are not necessarily consecutive.

The output unit 25 instead of the correction circuit 13 may correct the first pixel signal by using the second pixel signal.

Alternatively, the video-processing circuit 14 instead of the correction circuit 13 may correct the first pixel signal by using the second pixel signal.

As described above, the image sensor 10 (imaging device) includes the two or more pixels 26 disposed in a matrix shape. The photoelectric conversion element 260 of each of the pixels 26 performs photoelectric conversion and generates an electric charge in accordance with the amount of received light. The FD 262 of each of the pixels 26 holds the electric charge generated by the photoelectric conversion element 260. The transfer switch 261 of each of the pixels 26 transfers the electric charge generated by the photoelectric conversion element 260 to the FD 262. The reset switch 263 of each of the pixels 26 resets the electric charge held in the FD 262.

The state of each of the transfer switch 261 and the reset switch 263 is switchable between the ON state and the OFF state. An operation mode that is switchable between a first mode and a second mode is set in the image sensor 10. When the first mode is set in the image sensor 10 as the operation mode, at least one pixel 26 of the two or more pixels 26 sets the state of the transfer switch 261 to the ON state so as to transfer the electric charge to the FD 262 and outputs a first pixel signal in accordance with the electric charge held in the FD 262. After the first pixel signal is output, the at least one pixel 26 sets the state of the transfer switch 261 to the OFF state so as to stop transfer of the electric charge to the FD 262.

When the second mode is set in the image sensor 10 as the operation mode, the at least one pixel 26 sets the state of the reset switch 263 to the ON state so as to reset the electric charge held in the FD 262. The at least one pixel 26 fixes the state of the transfer switch 261 to the OFF state. The at least one pixel 26 outputs a second pixel signal in accordance with the electric charge held in the FD 262 in the output period SOUT. The state of the reset switch 263 in the at least one pixel 26 is fixed to the ON state in the output period SOUT.

An imaging method according to each aspect of the present invention includes first to fifth steps. When the first mode is set in the image sensor 10 as the operation mode, the image sensor 10 sets the state of the transfer switch 261 of at least one pixel 26 of the two or more pixels 26 to the ON state in the first step (timing T6) so as to transfer the electric charge to the FD 262. When the first mode is set in the image sensor 10 as the operation mode, the image sensor 10 outputs a first pixel signal in accordance with the electric charge held in the FD 262 of the at least one pixel 26 in the second step (timing T7). After the electric charge is transferred to the FD 262, the image sensor 10 sets the state of the transfer switch 261 of the at least one pixel 26 to the OFF state in the third step (timing T7) so as to stop transfer of the electric charge to the FD 262. When the second mode is set in the image sensor 10 as the operation mode, the image sensor 10 sets the state of the reset switch 263 of the at least one pixel 26 to the ON state in the fourth step (timing T10) so as to reset the electric charge held in the FD 262. The image sensor 10 outputs a second pixel signal in accordance with the electric charge held in the FD 262 in the fifth step (timing T10) in the output period SOUT. When the second mode is set in the image sensor 10 as the operation mode, the state of the transfer switch 261 of the at least one pixel 26 is fixed to the OFF state. The state of the reset switch 263 in the at least one pixel 26 is fixed to the ON state in the output period SOUT.

Each aspect of the present invention may include the following modified example. Each of the two or more pixels 26 includes the selection switch 265 that includes a gate terminal and outputs the first pixel signal or the second pixel signal when the selection control signal SEL (row selection signal) is input to the gate terminal.

Each aspect of the present invention may include the following modified example. Each column circuit 27 (signal-holding circuit) holds the second pixel signal. The output period SOUT includes a period during which each column circuit 27 holds the second pixel signal.

Each aspect of the present invention may include the following modified example. The state of the transfer switch 261 of the at least one pixel 26 is fixed to the OFF state in the output period SOUT.

Each aspect of the present invention may include the following modified example. Each of two or more vertical scanning periods of the image sensor 10 includes a first period during which the first mode is set in the image sensor 10 and a second period during which the second mode is set in the image sensor 10.

Each aspect of the present invention may include the following modified example. The second mode is set in the image sensor 10 in at least one vertical scanning period of the two or more vertical scanning periods of the image sensor 10.

Each aspect of the present invention may include the following modified example. An imaging system (camera unit 9) includes both the scope 8 to be inserted inside a living body and the image sensor 10. The image sensor 10 is disposed in the distal end 2b of the scope 8.

Each aspect of the present invention may include the following modified example. The correction circuit 13 receives the first pixel signal and the second pixel signal and corrects the first pixel signal by using the second pixel signal.

Each aspect of the present invention may include the following modified example. The correction circuit 13 corrects the first pixel signal by using the second pixel signal output from a pixel 26 disposed in at least one row among the two or more pixels 26.

The state of the reset switch 263 is fixed to the ON state in the output period SOUT. Even when strong light is incident on the imaging unit 20, each pixel 26 can output the same second pixel signal as that in a state in which no light is incident on the imaging unit 20. The correction circuit 13 can correct the first pixel signal by using the second pixel signal with high accuracy.

First Modified Example

A first modified example of the embodiment of the present invention will be described. In general, vertical-line-shaped noise occurs due to the variations of the characteristics of a column circuit in an image sensor of a column-parallel-reading system. The variations depend on a power source voltage and the temperature. In the first modified example, the correction circuit 13 corrects a first pixel signal in real time.

Figures 9, 10:
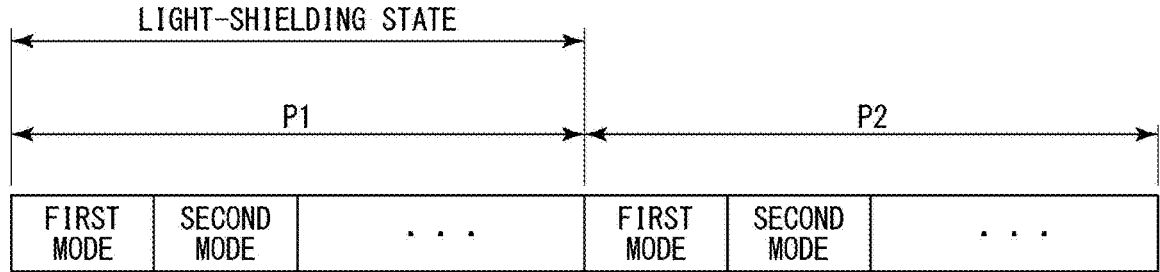
FIG. 9 is a diagram showing an example of a first pixel signal and a second pixel signal in a first modified example of the embodiment of the present invention.
FIG. 10 is a diagram showing an operation mode of an image sensor included in an endoscope system in a second modified example of the embodiment of the present invention.

FIG. 9 shows an example of a first pixel signal and a second pixel signal. A pixel signal (frame) generated in one vertical scanning period includes the first pixel signal and the second pixel signal. The correction circuit 13 uses at least part of a second pixel signal of an (n−1)-th frame in order to correct a first pixel signal of an n-th frame. In other words, the correction circuit 13 uses at least part of a second pixel signal of a frame immediately before a target frame in order to correct a first pixel signal of the target frame. The correction circuit 13 uses second pixel signals output from pixels 26 of one or more rows. In the example shown in FIG. 9, the correction circuit 13 uses second pixel signals output from pixels 26 of n rows. This n is variable.

The correction circuit 13 may use at least part of a second pixel signal of an n-th frame in order to correct a first pixel signal of the n-th frame. Alternatively, the correction circuit 13 may use at least part of a second pixel signal of an (n−1)-th frame and at least part of the second pixel signal of the n-th frame in order to correct the first pixel signal of the n-th frame.

The correction circuit 13 can reduce the noise generated due to the influence of the power source voltage VDD and the temperature by correcting a first pixel signal in real time.

Second Modified Example

A second modified example of the embodiment of the present invention will be described. The correction circuit 13 can eliminate the majority of the vertical-line-shaped noise by correcting a first pixel signal. However, part of the vertical-line-shaped noise remains in the method described above since a driving method of each pixel 26 for generating a first pixel signal and a driving method of each pixel 26 for generating a second pixel signal are different. In the second modified example, the correction circuit 13 eliminates such noise.

FIG. 10 shows an operation mode of the image sensor 10. The operation mode of the image sensor 10 in a first period P1 and a second period P2 is shown in FIG. 10.

The image sensor 10 is driven in a state in which no light is incident on the two or more pixels 26 in the first period P1. For example, the first period P1 is an inspection period before factory shipment. The first mode and the second mode are sequentially set in the image sensor 10, and the image sensor 10 sequentially outputs the first pixel signal and the second pixel signal. The correction circuit 13 corrects the first pixel signal by using the second pixel signal.

The correction circuit 13 calculates an arithmetic mean of first pixel signals that are generated in two or more vertical scanning periods and are corrected by using second pixel signals. By doing this, the correction circuit 13 generates a reference pixel signal. The number of first pixel signals used for generating the reference pixel signal is variable. It is preferable that the number is set such that random noise is sufficiently eliminated. The correction circuit 13 may perform median-filtering processing on the reference pixel signal in order to eliminate the influence of pixel defects.

Figure 11:
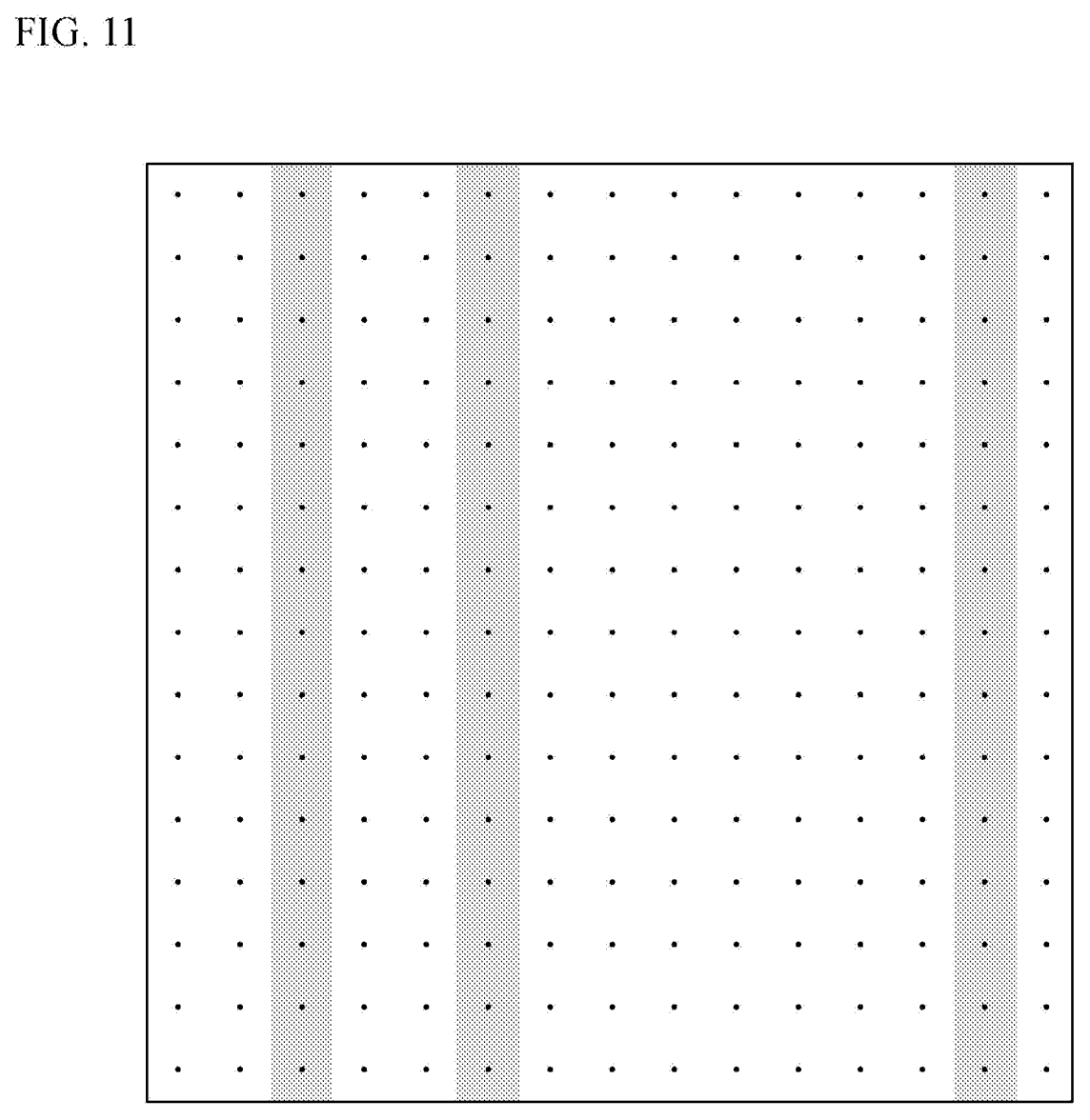

FIG. 11 shows an example of the reference pixel signal. Values of reference pixel signals corresponding to the first and second pixel signals output from pixels 26 of 15 rows and 15 columns are shown in FIG. 11. The reference pixel signals include vertical-line-shaped noise.

The correction circuit 13 calculates an average value Col2[x] of values of reference pixel signals of each column instead of the average value Col1[x] in accordance with Expression (1) described above. ImageArea2[x, y] in Expression (1) indicates a value of a reference pixel signal of a pixel 26 of the x-th column and the y-th row. The average value Col2[x] is stored on a memory of the connector unit 5.

The image sensor 10 is driven in a normal state in the second period P2. The first mode and the second mode are sequentially set in the image sensor 10, and the image sensor 10 sequentially outputs the first pixel signal and the second pixel signal. The correction circuit 13 corrects the first pixel signal by using the second pixel signal. Thereafter, the correction circuit 13 subtracts the average value Col2[x] from the value of the first pixel signal, thus correcting the first pixel signal.

Figure 12:
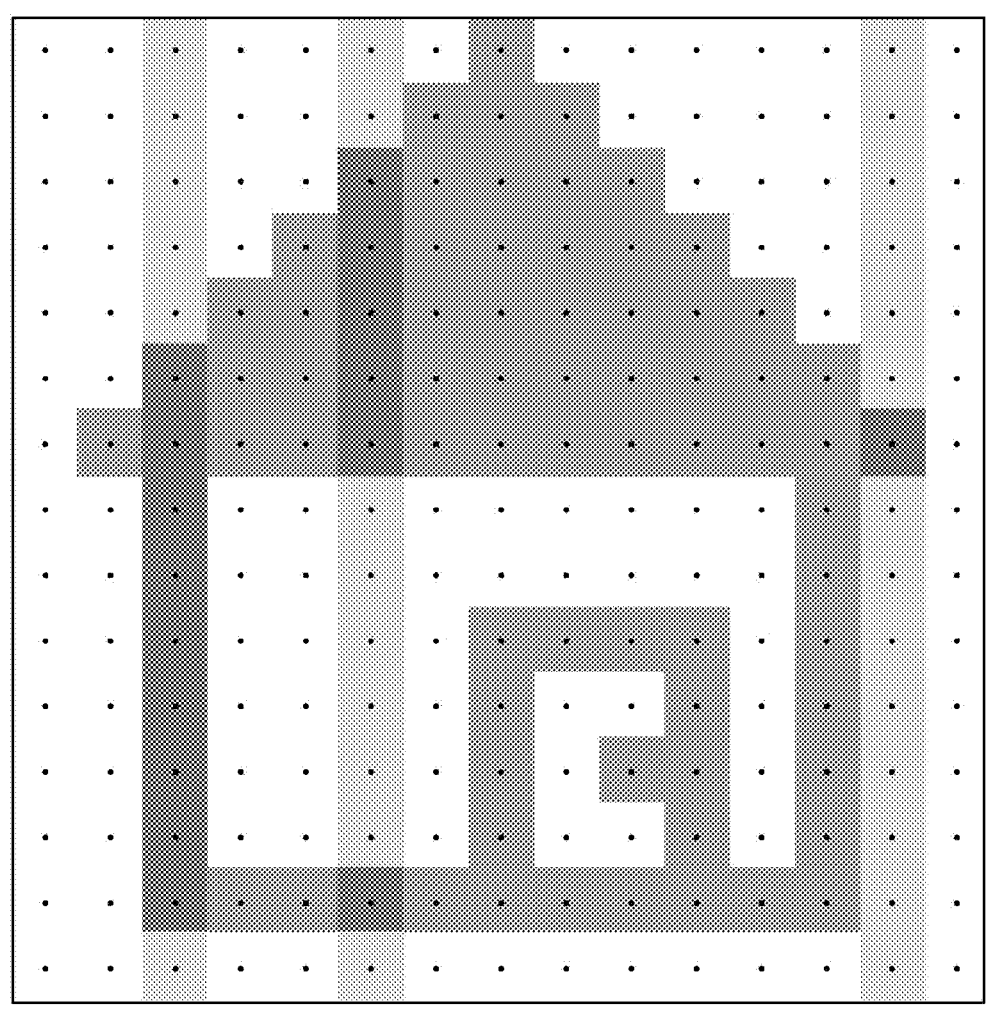
FIG. 12 is a diagram showing an example of a first pixel signal in the second modified example of the embodiment of the present invention.

FIG. 12 shows an example of the first pixel signal on which the correction using the second pixel signal has been performed. Values of first pixel signals output from pixels 26 of 15 rows and 15 columns are shown in FIG. 12. The correction circuit 13 subtracts the average value Col2[x] from the value of the first pixel signal shown in FIG. 12, thus calculating the value of the first pixel signal. The first pixel signal that has been corrected by using the average value Col2[x] is similar to that shown in FIG. 8 described above.

Each aspect of the present invention may include the following modified example. The correction circuit 13 receives a first pixel signal and a second pixel signal output from at least one pixel 26 in the first period P1 during which no light is incident on the two or more pixels 26. The correction circuit 13 receives a first pixel signal and a second pixel signal output from the at least one pixel 26 in the second period P2 different from the first period P1. The correction circuit 13 performs correction using the second pixel signal of the first period P1 on the first pixel signal of the first period P1, thus generating a reference pixel signal. The correction circuit 13 corrects the first pixel signal of the second period P2 by using the second pixel signal of the second period P2. The correction circuit 13 corrects the corrected first pixel signal of the second period P2 by using the reference pixel signal.

As described above, the correction circuit 13 corrects the first pixel signal by using the reference pixel signal after the first pixel signal is corrected by using the second pixel signal. Therefore, the correction circuit 13 can reduce the noise that occurs in accordance with the driving method of each pixel 26.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device, comprising multiple pixels disposed in a matrix shape, each of the pixels including:

a photoelectric conversion element configured to perform photoelectric conversion and generate an electric charge in accordance with an amount of received light;

a floating diffusion configured to hold the electric charge;

a transfer switch configured to transfer the electric charge generated by the photoelectric conversion element to the floating diffusion; and a reset switch configured to reset the electric charge held in the floating diffusion, wherein a state of each of the transfer switch and the reset switch is switchable between an ON state and an OFF state, wherein an operation mode that is switchable between a first mode and a second mode is set, wherein, when the first mode is set, at least one pixel sets a state of the transfer switch to the ON state so as to transfer the electric charge to the floating diffusion and outputs a first pixel signal in accordance with the electric charge held in the floating diffusion, wherein, after the electric charge is transferred to the floating diffusion, the at least one pixel sets the state of the transfer switch to the OFF state so as to stop transfer of the electric charge to the floating diffusion, wherein, when the second mode is set, the at least one pixel sets a state of the reset switch to the ON state so as to reset the electric charge held in the floating diffusion, fixes the state of the transfer switch to the OFF state, and outputs a second pixel signal in accordance with the electric charge held in the floating diffusion in an output period, and wherein the state of the reset switch in the at least one pixel is fixed to the ON state in the output period.

2. The imaging device according to claim 1, wherein each of the multiple pixels includes a selection switch that includes a gate terminal and is configured to output the first pixel signal or the second pixel signal when a row selection signal is input to the gate terminal.

3. The imaging device according to claim 1, comprising a signal-holding circuit configured to hold the second pixel signal, wherein the output period includes a period during which the signal-holding circuit holds the second pixel signal.

4. The imaging device according to claim 1, wherein the state in the transfer switch of the at least one pixel is fixed to the OFF state in the output period.

5. The imaging device according to claim 1, wherein each of two or more vertical scanning periods of the imaging device includes a first period during which the first mode is set and a second period during which the second mode is set.

6. The imaging device according to claim 1, wherein the second mode is set in at least one vertical scanning period of two or more vertical scanning periods of the imaging device.

7. An endoscope, comprising:

a scope to be inserted into a living body; and the imaging device according to claim 1, wherein the imaging device is disposed in a distal end of the scope.

8. An imaging system, comprising:

the imaging device according to claim 1; and a correction circuit configured to receive the first pixel signal and the second pixel signal and correct the first pixel signal by using the second pixel signal.

9. The imaging system according to claim 8, wherein the correction circuit is configured to:

receive the first pixel signal and the second pixel signal output from the at least one pixel in a first period during which no light is incident on the multiple pixels;

receive the first pixel signal and the second pixel signal output from the at least one pixel in a second period different from the first period;

perform correction using the second pixel signal of the first period on the first pixel signal of the first period so as to generate a reference pixel signal;

correct the first pixel signal of the second period by using the second pixel signal of the second period; and correct the corrected first pixel signal of the second period by using the reference pixel signal.

10. The imaging system according to claim 8, wherein the correction circuit is configured to correct the first pixel signal by using the second pixel signal output from a pixel disposed in at least one row among the multiple pixels.

11. An imaging method using an imaging device that includes multiple pixels disposed in a matrix shape, the imaging method comprising an imaging step, wherein each of the multiple pixels includes:

a photoelectric conversion element configured to perform photoelectric conversion and generate an electric charge in accordance with an amount of received light;

a floating diffusion configured to hold the electric charge;

a transfer switch configured to transfer the electric charge generated by the photoelectric conversion element to the floating diffusion; and a reset switch configured to reset the electric charge held in the floating diffusion, wherein a state of each of the transfer switch and the reset switch is switchable between an ON state and an OFF state, wherein an operation mode that is switchable between a first mode and a second mode is set, wherein the imaging step includes:

setting a state of the transfer switch of at least one pixel to the ON state so as to transfer the electric charge to the floating diffusion when the first mode is set;

outputting a first pixel signal in accordance with the electric charge held in the floating diffusion when the first mode is set;

setting the state of the transfer switch of the at least one pixel to the OFF state so as to stop transfer of the electric charge to the floating diffusion after the electric charge is transferred to the floating diffusion;

setting a state of the reset switch of the at least one pixel to the ON state so as to reset the electric charge held in the floating diffusion when the second mode is set; and outputting a second pixel signal in accordance with the electric charge held in the floating diffusion in an output period, wherein, when the second mode is set, the state of the transfer switch of the at least one pixel is fixed to the OFF state, and wherein the state of the reset switch in the at least one pixel is fixed to the ON state in the output period.

* * * * *